United States Patent [19]

Keller et al.

[11] 4,351,776

[45] Sep. 28, 1982

[54] PREPARATION OF IODOPHTHALONITRILE

[75] Inventors: Teddy M. Keller, Alexandria, Va.; James R. Griffith, Riverdale Heights, Md.

[73] Assignee: The United States of America as represented by the Secretary of the Navy, Washington, D.C.

[21] Appl. No.: 195,999

[22] Filed: Oct. 8, 1980

Related U.S. Application Data

[63] Continuation of Ser. No. 78,402, Sep. 24, 1979, abandoned.

[51] Int. Cl.$^3$ ........................................... C07C 121/56
[52] U.S. Cl. .............................. 260/465 G; 260/314.5
[58] Field of Search .............. 260/314.5, 465 H, 465 G

[56] References Cited

U.S. PATENT DOCUMENTS 2,225,441  12/1940  Braun et al. ...................... 260/314.5
3,763,182  10/1973  Horiguchi et al. ................ 260/314.5
4,209,458   6/1980  Keller ............................... 260/465 F

OTHER PUBLICATIONS

Inuka et al., Chem. Abstracts, vol. 63, col. 2913 b (1965), (Abst. of Kogyo Kagaku Zasshi vol. 68, pp. 315-318 (1965)).

Maki et al., Chem. Abstracts, vol. 63, cols. 18316 to 18317 (1965), (Abst. of Japanese Patent 11,750 ('65)).

Arai et al., Chem. Abst., vol. 70, Abst. No. 69295n (1969), (Abst. of Japanese Patent 19,225 (1968)).

Suzuki et al., Chem. Abst., vol. 72, Abst. 33,223q (1970), (Abst. of Kogyo Kagaku Zasshi vol. 72, pp. 712-716, (1969)).

Suzuki et al., Kogyo Kagaku Zasshi, vol. 72, pp. 712-716 (1969).

Oksengendler et al., Chem. Abstracts, vol. 87, Abst. No. 137296s (1977), (Abst. of Zh. ORg. Khim, vol. 13, pp. 1554-1558, (1977)).

Oksengendler et al., Chem. Abstracts, vol. 88, Abst. 89322u (1978), (Abst. of Zhur. Org. Khim, vol. 13, p. 2234 (1977)).

Chem. Abstracts, vol. 88, Subject Index A-B, p. 599 CS (1978).

Primary Examiner—Dolph H. Torrence
Attorney, Agent, or Firm—Robert F. Beers; William T. Ellis; Thomas E. McDonnell

[57] ABSTRACT

Iodophthalonitrile is prepared by mixing aminophthalonitrile with sulfuric acid at a temperature below 25° C., reacting that product with sodium nitrite at a temperature below 15° C., and reacting that product with potassium iodide at a temperature below 20° C. A fluoroalkyl phthalonitrile is prepared by mixing fluoroalkyl iodide, activated copper, iodophthalonitrile, and a solvent under an inert atmosphere at a temperature from 110° C. to 125° C. at least until the solution turns green. Both compounds are useful in synthesizing phthalocyanines and polyphthalocyanines.

4 Claims, No Drawings

PREPARATION OF IODOPHTHALONITRILE

This is a continuation of application Ser. No. 78,402, filed Sept. 24, 1979, abandoned.

BACKGROUND OF THE INVENTION

The invention pertains generally to substituted aromatic nitrile synthesis and particularly to the specific substitution of the phthalonitrile ring with an iodo-group or a fluoroalkyl group.

Polyphthalocyanines have become an important structural material, possessing many properties superior to polyimides and epoxies. Presently, these compounds are prepared by polymerizing bisorthodinitriles, which are structurally two phthalonitriles connected by a bridging group. It is the bridging group that determines, to a major degree, the properties of the resulting polymer. Many excellent possible bridging groups are fluorinated which makes the synthesis of bisorthodinitriles with these groups unlikely by existing methods, such as a nucleophilic displacement of the nitro group of nitrophthalonitrile. An iodocoupling reaction may provide a synthesis for fluorocarbonbridged bisorthodinitriles, but the necessary iodo-compounds have not been prepared.

Several problems exist with the synthesis of these iodo-compounds. Due to the strong electron acceptance of iodine, this halogen, unlike bromine or chlorine, forms complexes with aromatic compounds when reacted directly with them. A substituted aromatic ring, such as the phthalocyanine ring, is difficult to substitute at a specific position with a fluorocarbon group due to the fluorocarbon being a very weak nucleophile.

A specific fluoroalkyl substitution on the phthalonitrile ring has importance besides the synthesis of fluorocarbon-bridged polyphthalocyanines. The specific substitution allows greater control of the properties and costs of fluorocarbon-substituted phthalocyanines which are formed from phthalonitriles.

SUMMARY OF THE INVENTION

It is, therefore, an object of the present invention to provide a synthesis for iodophthalonitrile and fluorocarbon phthalonitriles.

A further object of this invention is to monosubstitute the phthalonitrile ring at a specific location with iodine or a wide range of fluoroalkyls, including perfluorinated alkyls.

These and other objects are achieved by the iodosubstitution of aminophthalonitrile in a strongly acidic solution to form iodophthalonitrile and by the iodo-coupling reaction between iodophthalonitrile and an iodo-fluoroalkane in the presence of activated copper.

DETAILED DESCRIPTION OF THE INVENTION

Mono-substituted phthalonitriles of the present invention can be represented by the formula:

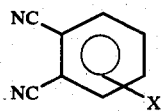

wherein X is an iodo-or fluoroalkyl group. The fluoroalkyl may have any degree of fluorination and chain length. If the fluoroalkyl is branched, the α-carbon cannot be branched because of steric hindrance with the placement of the group on the ring by the side chains. Preferably, the fluoroalkyl has from 2 to 20 carbon in the backbone chain and if the fluoroalkyl is branched, it has from 1 to 4 side chains of 1 to 4 carbon atoms. More preferably, the fluoroalkyl has from 2 to 10 carbon atoms in the backbone chain and if the fluoroalkyl is branched, it has from 1 to 3 side chains of 1 to 3 carbon atoms. If the α-carbon does not have two fluoride atoms, the yield is reduced on account of instability of the organo-copper intermediate which is not perfluorinated at the α-carbon. Due to advantageous properties imparted to a compound by fluorine substitution it is preferred that the fluoroalkyl is perfluorinated. It is preferred that the α-carbon has one fluorine and is most preferred that the α-carbon has two fluorines.

In preparing iodophthalonitrile (X=I), 3 or 4-aminophthalonitrile is slowly admixed with a 40 to 60 weight-percent excess of concentrated sulfuric acid (18 M) at a temperature from 0° to 25° C. Mixing is continued until the reaction is complete as evidenced by the homogeneity of the reaction. After the temperature is reduced to about −10° C. to about 15° C., the product, amine bisulfate, is precipitated from solution by slowly adding cold water to the reaction medium. It is critical that the temperature does not exceed about 25° C. during the addition of water, otherwise the cyanide groups may be oxidized to carboxylic groups. Preferably, the temperature is maintained from 0° C. to 10° C.

Upon precipitation, anhydrous sodium nitrite dissolved in water is slowly added in a stoichiometric amount (one mole for each mole of bisulfate) to the reaction medium. Care should be taken to keep the temperature from 0° to 20° C. and preferably between 0° to 10° C. A diazonium salt solution is formed immediately and is then admixed with an aqueous solution of potassium iodide, potassium iodide being present in a 50 mole-percent excess. Mixing is continued at a temperature from 0° to 20° C. until the reaction is complete, as evidenced by the cessation of nitrogen gas evolution.

The product, iodophthalonitrile is separated by suction filtration, and washed, in sequence, with a ten-percent aqueous sodium bisulfite solution, with a saturated aqueous sodium bircarbonate solution, and with water. Finally, the product is dissolved in an ethanol-water solution and recrystalized.

The fluoroalkyl phthalonitrile is prepared by an iodocoupling reaction which comprises reacting iodophthalonitrile, and iodo-fluoroalkane and activated copper (oxide-free copper) in dry dimethyl sulfoxide (DMSO) at an elevated temperature under argon. It is critical that the temperature is above 100° C. and the atmosphere is non-oxidizing.

A phthalocyanine of the general formula:

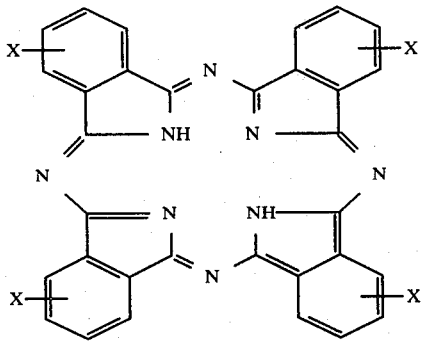

wherein X represents I or a fluoroalkyl can be prepared from the phthalonitriles of this invention. A phthalocyanine can be prepared from a fluoroalkyl phthalonitrile by heating a phthalonitrile at an elevated temperature, generally from 150° to 200° C. To prepare a phthalocyanine pigment from iodophthalonitrile, the nitrile is admixed with sodium hydride (NaH) in benzyl alcohol at a temperature from 140° to 180° C. and the product is quenched in methanol. Further details concerning the preparation of these phthalonitriles and phthalocyanines are disclosed in Keller, Teddy M. and Griffith, James R. *The Synthesis of A Fluorinated Phthalocyanine.* In J. Fl. Chem. 13:p. 73–77, 1979 which is incorporated herein by reference.

This phthalocyanine like other phthalocyanines can coordinate with a salt or metal by simply mixing in a metal or salt with the phthalonitrile and heating as before. Often the metal or salt accelerates the phthalocyanine formation reaction.

The preferred metals are copper, iron, zinc, and nickel on account of their enhancement of thermal stability over other metals at temperatures in excess of 250° C. Examples of other metals which may be used are chromium, molybdenum, vanadium, beryllium, silver, mercury, tin, lead, antimony, calcium, barium, manganese, magnesium, cobalt, palladium and platinum. Suitable metallic salts include cuprous bromide, cuprous cyanide, cuprous ferricyanide, zinc chloride, zinc bromide, zinc iodide, zinc ferrocyanide, zinc acetate, zinc sulfide, silver chloride, stannous chloride, ferrous chloride, ferric chloride, ferrous ferricyanide, ferrous chloroplatinate, ferrous fluoride, ferrous sulfate, cobaltous chloride, cobaltic sulfate, cobaltous cyanide, nickel chloride, nickel cyanide, nickel sulfate, nickel carbonate, stannic chloride, stannous chloride hydrate, a complex of triphenylphosphine oxide and mixtures thereof. Additional examples of metals and salts are found in Mosher, Frank H. and Thomas, Arthur L. *Phthalocyanine Compounds,* N.Y. Reinbold, 1963, pp. 104–141.

The phthalocyanines of the present invention can be conveniently represented as $PcX_4$ if neat, as $M.PcX_4$ if coordinated with a metal, and $MX.PcX_4$ wherein, Pc represents a phthalocyanine nucleus, X represents iodo or a fluoroalkyl group, M is a metal, and MX is a salt.

A fluoroalkyl bisorthodinitrile is prepared by a iodocoupling reaction which comprises reacting diiodofluoroalkyl with iodophthalonitrile in the presence of a metallic coupling agent, e.g., activated copper, in a dry polar aprotic solvent, e.g., DMSO at an elevated temperature, e.g., 115° C. A polyphthalocyanine is prepared by heating the bisorthodinitrile at a temperature from 200° C. to 250° C. Further details concerning the preparation of bisorthodinitriles from iodophthalonitrile and the polymerization of these dinitriles are in U.S. patent application Ser. No. 26,863, filed on Apr. 4, 1979 by Teddy M. Keller and James R. Griffith, now U.S. Pat. No. 4,209,458 issued on June 24, 1980.

The following examples illustrate the practice of the present invention. It is understood that these examples are given by way of illustration and are not meant to limit this disclosure or the claims to follow in any manner.

EXAMPLE I

Synthesis of 4-Iodophthalonitrile

4-Aminophthalonitrile (40 g, 0.28 mol) was slowly added to 80 ml of concentrated sulfuric acid and the mixture was stirred with cooling (below 25° C.) until dissolution was complete. After cooling below 15° C., ice water (175 ml) was slowly added to precipitate the amine bisulfate. A solution of sodium nitrite (20 g, 0.29 mol) in 40 ml of water was then added at such a rate as to maintain the temperature at 0°–10° C. After stirring the solution for an additional 15 minutes, a few crystals of urea were added to decompose any excess sodium nitrite. The homogeneous solution was then poured into a beaker containing potassium iodide (75 g, 0.45 mol) dissolved in 150 ml of water. After the evolution of nitrogen had ceased and a negative test with alkaline p-methoxyphenol indicated that the reaction was complete, the brown precipitate was collected by suction filtration and washed with 10% sodium bisulfite, with saturated sodium bicarbonate and finally with water. Recrystallization from ethanol-water afforded 51 g (72%) of product of 3, m.p. 141°–142° C.; ir (KBr) 3098–3010 (—CH), 2240 (CN) and 1577 cm$^{-1}$(C≡C).

Anal. Calcd. for $C_8H_3N_2I$: C, 37.82; H, 1.19; N, 11.03; I, 49.96 Found: C, 37.83; H, 1.21; N, 10.85; I, 50.11.

EXAMPLE II

Preparation of 4-Perfluoroheptylphthalonitrile

A mixture of perfluoroheptyl iodode (4.0 g, 8.1 mmol), activated copper (1.3 g, 20 mg. atom), 4-iodophthalonitrile (1.9 g, 7.5 mmol) and 11 ml of dry DMSO was purged for 15 minutes with argon and then heated for 2 hours at 115°–120° C. under an argon atmosphere. At prolonged reaction times, the mixture turned green. After cooling the content was poured into 75 ml of ice water and extracted with three 25-ml portions of ether. The combined ethereal extract was washed three times with water, charcoaled dried over anhydrous sodium sulfate, and concentrated to afford 2.1 g (56%) of product of 1 m.p. 98°–99° C.; ir (KBr) 3110–3050 (═CH), 2242 (CN), 1608 (very weak, C═C) and 1280–1100 cm$^{-1}$ (CF).

Anal. Calcd. for $C_{15}H_3F_{15}N_2$: C, 36.31; H, 0.61; F, 57.44; N, 5.65. Found: C, 36.38; H, 0.69; F, 57.65; N, 5.71.

EXAMPLE III

Phthalocyanine Formation

4-Perfluoroheptylphthalonitrile (0.1 g, 0.2 mmol) was placed in a small test tube and slowly heated to 170° C. which caused the sample to darken. After 4 hours at 170° C., the sample was then heated at 200° C. for 18 hours which resulted in the evaporation of the material. Only a thin film remained.

EXAMPLE IV

SnCl$_2$-Phthalocyanine Formation

Another sample of 4-perfluoroheptylphthalonitrile (0.1 g, 0.2 mmol) and stannous chloride dihydrate (0.11 g, 0.49 mmol) were heated to 165°–170° C. where homogeneity occured. After 4 hours at 170° C., the melt was heated at 200° C. for 18 hours which resulted in solidfication. The blue color and the absence of any cyano absorption (2242 cr.$^{-1}$) were taken as evidence that phthalocyanine formation had taken place.

EXAMPLE V

Formation of Polyphthalocyanine 1,3-Bis(3,4-dicyanophenyl)-perfluoropropane (0.25 g, 0.6 mmol) and stannous chloride dihydrate (0.07 g, 0.3 mmol) were placed in a test tube and slowly heated to 130° C. where the monomer melted. At 140° C., homogeneity occurred and the sample started to darken almost immediately. The sample was heated at 200° C. for 10 hours and postcured at 220° C. for 24 hours.

Obviously many modifications and variations of the present invention are possible in light of the above teachings. It is therefore to be understood that within the scope of the appended claims the invention may be practiced otherwise than as specifically described.

What is claimed and desired to be secured by Letters Patent of the United States is:

1. A process of making iodophthalonitrile comprising:
   mixing an aminophthalonitrile with an excess of H$_2$SO$_4$ at a temperature of about 0° C. to 25° C. until the resultant reaction is substantially complete;
   cooling the solution to below about 15° C.;
   adding cold water to said solution at a solution temperature below 25° C. to produce amine bisulfate;
   adding aqueous NaNO$_2$ to said solution at a solution temperature of about 0° C. to 20° C. to produce a diazonium salt solution;
   mixing said diazonium salt solution with an excess of KI until the resulting reaction is substantially complete;
   separating and purifying the resultant reaction product, iodophthalonitrile, from said solution.

2. A process as claimed in claim 1 wherein the aminophthalonitrile is 3 or 4-aminophthalonitrile.

3. A process as claimed in claim 2 where the temperature of the mixture during precipitation of amine disulfate is maintained from 0° C. to 10° C.

4. A process as claimed in claim 1 where aqueous NaNO$_2$ is added in a substantially stoichiometric amount at a mixture temperature of 0° C. to 10° C.

* * * * *